(12) United States Patent
Rasche et al.

(10) Patent No.: US 11,116,444 B2
(45) Date of Patent: Sep. 14, 2021

(54) METHOD FOR DETECTING THE MOVEMENT OF A TEMPOROMANDIBULAR JOINT

(71) Applicant: DENTSPLY SIRONA inc., York, PA (US)

(72) Inventors: Volker Rasche, Erbach (DE); Stefan Wundrak, Bensheim (DE)

(73) Assignee: DENTSPLY SIRONA Inc., York, PA (US)

( * ) Notice: Subject to any disclaimer, the term of this patent is extended or adjusted under 35 U.S.C. 154(b) by 310 days.

(21) Appl. No.: 16/466,316

(22) PCT Filed: Dec. 6, 2017

(86) PCT No.: PCT/EP2017/081641
§ 371 (c)(1),
(2) Date: Jun. 4, 2019

(87) PCT Pub. No.: WO2018/104372
PCT Pub. Date: Jun. 14, 2018

(65) Prior Publication Data
US 2019/0290190 A1   Sep. 26, 2019

(30) Foreign Application Priority Data
Dec. 6, 2016   (DE) .......................... 102016224182.6

(51) Int. Cl.
*A61B 5/00* (2006.01)
*A61B 90/00* (2016.01)
(Continued)

(52) U.S. Cl.
CPC ............ *A61B 5/4542* (2013.01); *A61B 5/004* (2013.01); *A61B 5/055* (2013.01); *A61B 5/1122* (2013.01);
(Continued)

(58) Field of Classification Search
CPC ........ A61B 5/4542; A61B 5/004; A61B 5/055
See application file for complete search history.

(56) References Cited

U.S. PATENT DOCUMENTS

| 10,127,347 B2 | 11/2018 | Klein |
| 10,234,529 B2 | 3/2019 | Rasche |
| 10,362,966 B2 | 7/2019 | Kruger |

FOREIGN PATENT DOCUMENTS

| DE | 102009027356 A1 | 12/2010 |
| WO | 2005079699 A1 | 9/2005 |

(Continued)

OTHER PUBLICATIONS

International Search Report; PCT/EP2017/081641; Jan. 25, 2018 (completed); dated Feb. 7, 2018 (mailed).
(Continued)

*Primary Examiner* — Joseph M Santos Rodriguez
(74) *Attorney, Agent, or Firm* — DENTSPLY SIRONA Inc.

(57) ABSTRACT

Described is a method for detecting and displaying the movement of a temporomandibular joint which connects a lower jaw and an upper jaw by magnetic resonance imaging. A marker is secured to the lower jaw, a marker movement curve is generated using magnetic resonance imaging measurement data sets during a first measurement interval, during which the lower jaw is moved relative to the upper jaw, and a point which corresponds to a first position of the lower jaw relative to the upper jaw is ascertained on the movement curve. An image data set is generated during a second measurement interval, during which the temporomandibular joint is not moved, and a first model, which represents at least one part of the upper jaw and/or a temporal bone part that comprises the temporomandibular joint socket, and a second model, which represents at least one part of the lower jaw, are ascertained therefrom. A (Continued)

movement curve of the second model relative to the first model is calculated and displayed using the marker movement curve.

13 Claims, 2 Drawing Sheets

(51) Int. Cl.
    *A61B 5/055*     (2006.01)
    *A61B 5/11*      (2006.01)
    *A61B 6/00*      (2006.01)
    *A61C 19/045*    (2006.01)
    *G01R 33/56*     (2006.01)
    *G01R 33/563*    (2006.01)
    *G01R 33/58*     (2006.01)

(52) U.S. Cl.
    CPC ............ *A61B 5/1127* (2013.01); *A61B 6/505* (2013.01); *A61B 90/39* (2016.02); *A61C 19/045* (2013.01); *G01R 33/5608* (2013.01); *G01R 33/56308* (2013.01); *G01R 33/58* (2013.01); *A61B 2090/3933* (2016.02); *A61B 2090/3958* (2016.02); *A61B 2090/3966* (2016.02); *A61B 2090/3991* (2016.02)

(56) References Cited

FOREIGN PATENT DOCUMENTS

WO    2009118391 A1    10/2009
WO    2016016839 A1    2/2016

OTHER PUBLICATIONS

Written Opinion of the International Searching Authority; PCT/EP2017/081641; Jan. 25, 2018 (completed); dated Feb. 7, 2018 (mailed).

International Preliminary Report on Patentability; PCT/EP2017/081641; dated Jun. 11, 2019 (date of issuance).

"Real-Time Magnetic Resonance Imaging of Temporomandibular Joint Dynamics"; The Open Medical Imaging Journal; vol. 5, pp. 1-7; Jan. 1, 2011; Shuo Zhang et al.

Prospective Real Time Head Motion Correction Using Inductively Coupled Wireless NMR Probes'; Magn. Resort Med (2014), pp. 971-985; S. Sengupta et al.

METHOD FOR DETECTING THE MOVEMENT OF A TEMPOROMANDIBULAR JOINT

TECHNICAL FIELD

The invention relates to a method for detecting and displaying the movement of a temporomandibular joint of a patient, which connects a lower jaw and an upper jaw, by means of magnetic resonance imaging.

STATE OF THE ART

Typical methods for detecting and visualizing the movement of a temporomandibular joint, such as those used for the diagnosis of craniomandibular dysfunctions, for example, combine movement data from an axiography scan with the image data of a DVT scan. The thus obtained visualization is frequently also supplemented with the data of a surface scan.

Disadvantageous, however, is the radiation exposure from a DVT scan, the inability of the DVT scan to display soft tissue and the large amount of time required.

A method for tracking the head movement of a patient during an MRI scan of the head, in which inductively coupling marker coils are used, is known from "Prospective Real Time Head Motion Correction Using Inductively Coupled Wireless NMR Probes," S. Sengupta et al., Magn. Reson. Med. (2014) 72(4), 971-985.

With that in mind, the object of the invention is to further develop the state of the art and provide a method for a simple and quick detection and display of the movement of a temporomandibular joint using magnetic resonance imaging measurement.

PRESENTATION OF THE INVENTION

One subject matter of the invention is a method for detecting and displaying the movement of a temporomandibular joint of a patient, which connects a lower jaw and an upper jaw, by means of magnetic resonance imaging, wherein at least one marker that is visible to magnetic resonance imaging is secured to the lower jaw of the patient by means of a securing means.

A plurality of magnetic resonance imaging measurement data sets of a recording volume are generated in chronological succession during a first measurement time interval, wherein at least the temporomandibular joint, and/or at least a part of the lower jaw, as well as the at least one marker are positioned within the recording volume during the first measurement time interval, the lower jaw executes a movement relative to the upper jaw during the first measurement time interval and the movement of the lower jaw involves a first position relative to the upper jaw.

One at least two-dimensional marker position of the at least one marker in the recording volume is determined in each measurement data set and a marker movement curve is produced on the basis of the determined marker positions, wherein a point on the marker movement curve corresponding to the first position of the lower jaw relative to the upper jaw is identified.

At least one image data set of the recording volume is generated during a second measurement time interval, wherein at least the temporomandibular joint, and/or at least a part of the lower jaw, as well as the at least one marker are positioned within the recording volume during the second measurement time interval and, during the second measurement time interval, the lower jaw is in the first position relative to the upper jaw.

A first model and a second model are identified from the image data set, wherein the first model displays at least a part of the upper jaw and/or a part of the temporal bone that comprises the temporomandibular joint socket, also known as the fossa mandibularis, and the second model displays at least a part of the lower jaw. A relative position of the marker to the first model and to the second model is furthermore determined from the image data set.

A movement path of the second model relative to the first model is calculated and displayed on the basis of the marker movement curve and the relative position of the first model and the second model to the marker.

It goes without saying that the method step of positioning the marker is carried out prior to the first and the second measurement time interval, i.e. prior to the generation of the first measurement data sets and the image data set.

It is also goes without saying that, in terms of time, the first measurement time interval can be before or even after the second measurement time interval.

The movement of the temporomandibular joint is a chewing movement or a periodic opening and closing of the mouth or any other jaw movement carried out during the first measurement time interval.

The first position of the lower jaw relative to the upper jaw is the natural terminal occlusion, for example, or a position encoded by a dental impression. The first position can be determined in the movement curve and can also be reliably reproduced for the generation of the image data set.

Accordingly, the relative position of the first model and the second model to the marker in the first position is obtained from the image data set that is generated in said first position when the jaw is not moving, e.g. the terminal occlusion. It is goes without saying that the relative position of the one model to the marker is determined as well, when the relative position of the one model to the other model and the relative position of the other model to the marker are identified. The movement from the marker movement curve can be transferred to a movement of the second model, e.g. the lower jaw, relative to the first model, e.g. the upper jaw, on the basis of the relative position of the marker to the second and the second model in the first position and the point on the marker movement curve corresponding to the first position.

The marker visible to magnetic resonance imaging includes any marker capable of being uniquely identified in data acquired by means of magnetic resonance imaging.

In each case, the measurement data sets generated during the first measurement time interval are used only to determine the at least two-dimensional, preferably three-dimensional, position of the marker in the recording volume at the time of generation of the respective measurement data set. The measurement data sets are not used for the visual acquisition of the recording volume, i.e. the lower jaw, upper jaw and/or marker.

Correspondingly, the measurement data sets are any measurement data sets that can be generated by means of magnetic resonance imaging and provide information about the position of the marker. Individual magnetic resonance imaging projection images, for example, are sufficient for this purpose, wherein a data volume acquired along a k-space trajectory in the course of a measurement sequence is referred to as a projection image. The trajectories scanned to determine a marker position are preferably aligned orthogonally to one another. The measurement data sets respectively correspond to a radial scan along a radial beam, i.e. a so-called spoke within the recording volume, for example, or the data acquired during the scan, wherein such a scan typically only takes about 1 to 5 ms.

The time required for generating a measurement data set is consequently very short, in particular in comparison to the time required for generating an image data set, which makes it possible to record a large number of measurement data sets in quick succession and thus acquire the movement of the marker attached to the lower jaw, i.e. different marker positions, with high temporal resolution. The marker positions respectively identified from the individual measurement data sets are combined to a marker movement curve. It goes without saying that any, or at least any suitable, marker positions, or a suitable selection of marker positions, are used for this purpose.

During the first measurement time interval, information about the movement of the temporomandibular joint is obtained independent of a visual display, i.e. an acquisition of image information.

A visual display of at least a part of the jaw region is acquired as an image data set during the second measurement time interval. The image data set can be acquired using any known imaging method, e.g. using a magnetic resonance imaging method that is capable of recording at least parts of the jaw and/or the temporomandibular joint, in each case with teeth and gums and/or bones, and the marker in at least two, preferably three, dimensions.

A first model and a second model are extracted from the image data set, for example by means of segmentation. The first model comprises the upper jaw or a part of the upper jaw and/or a part of the temporal bone, e.g. the joint-forming socket, also referred to as the glenoid cavity or fossa mandibularis. The second model comprises the lower jaw or a part of the lower jaw, e.g. the joint-forming roller-shaped condyle of the lower jaw (caput mandibulae). The first and the second model are at least two-dimensional, preferably three-dimensional.

The movement of the temporomandibular joint is then visualized by a movement of the second model relative to the first model image, whereby movement data is taken from the movement curve.

Therefore, to show the movement of the jaw, a static visual display of the jaw, i.e. the image data set, is segmented into an upper and a lower region, e.g. the upper jaw and the lower jaw, and the lower region is then moved relative to the upper region according to the identified movement curve of the marker.

It goes without saying that the visualization can be carried out in the form of a video, with superimposed images or in any other form.

One advantage of the acquisition of temporomandibular joint movements according to the invention is that movement data and image data are acquired in separate method steps. The method steps can thus be adapted to the respective different requirements. It is in particular possible to select methods that are optimized with respect to time and/or data quality and/or radiation exposure.

Each measurement data set advantageously comprises at least three 1D projection images or at least two 2D projection images. It is therefore possible to quickly and easily determine the marker position on the basis of only two or three projection images, e.g. as a solution of a correspondingly compiled set equation.

According to an alternative embodiment, each first measurement data set comprises exactly one 1D projection, whereby one respective marker position is identified on the basis of at least two measurement data sets.

In advantageous embodiments, the at least one image data set is generated by means of magnetic resonance imaging, radiographically or also optically, whereby, in the case of radiographic generation, the at least one marker is radiopaque in at least in a region that is known with regard to its position and, in the case of optical generation, said marker is uniquely optically identifiable.

If the at least one image data set is generated with the magnetic resonance imaging device used for generating the measurement data sets, there is no need for an additional device for generating the image data set. This means that there is also the option of not having to reposition a patient for the generation of the image data set. The generation of the image data using magnetic resonance imaging further ensures a good visualization of soft tissues and good visibility of the discus articularis. In addition, when using the same recording device, it is possible to determine a three-dimensional position of the marker in the recording volume for the image data set as well, and use it for the transfer of the marker movement curve to the movement of the lower jaw.

A large number of projection images or k-space profiles, for example 200×200, from which the image data set is generated, are typically needed for a magnetic resonance image data set, i.e. a visual display or a two-dimensional or three-dimensional static model of at least a part of a jaw region.

The image data set can also be generated using an optical measurement of the lower jaw, the upper jaw and the at least one positioned marker, e.g. by means of an intraoral camera. A combination of magnetic resonance imaging and optical measurement results for the image data set is possible as well. Optical measurement data permits a very high spatial resolution of the tooth surface as well as more extensive forms of therapy, such as the production of dental splints.

It is also possible to generate the image data set completely or in part from radiographic measurement data.

The at least one marker is advantageously a magnetic resonance imaging active or a magnetic resonance imaging semi-active marker, particularly advantageously a coil or a combination of a coil and a liquid-filled body disposed within the coil, whereby the liquid is preferably doped with a contrast agent.

A semi-active marker is a device that is inductively coupled into the receiving system, for example a resonant circuit with a microcoil and a body that is disposed within the microcoil and filled with a doped liquid, whereas an active marker comprises a receiving coil connected to a separate receiving channel. The semi-active marker provides a particularly clear signal due to the increase in the effective flux and flip angle within the microcoil, which can be detected with the aid of a receiving coil of the MRI system. Using the active marker, the position information is recorded independent of the receiving coil of the MRI system.

The generation of a measurement data set for determining the position of a semi-active marker includes a measurement sequence with a flip angle of a few degrees, for example, whereby the semi-active marker locally intensifies the B1+ field, i.e. locally increases the flip angle. The semi-active marker thus provides a significantly amplified signal in comparison to the rest of the field of view, so that a position determination can be carried out easily and very reliably.

If a magnetic resonance imaging active marker is used, the measurement data sets are acquired directly using the active marker, whereas, in the case of a generation by means of magnetic resonance imaging, the image data set is identified with the aid of a receiving coil of the magnetic resonance imagining device being used.

The strength of the measurable signal is amplified by the doped liquid in the center of the coil. A precise position determination, or a movement tracking that is as precise as possible, can be carried out by determining the respective position of the center of gravity of the body in the measurement data sets, for example.

In order to permit a quick and simple determination of the three-dimensional position of the marker, the at least one marker advantageously comprises a three-dimensionally unique structure, e.g. a cross.

The at least one marker is advantageously positioned outside the oral cavity of the patient. According to an alternative embodiment, the at least one marker is placed within the oral cavity of a patient on a surface of at least one tooth, e.g. on a lingual surface of one or more incisors or on an oral surface of one or more molars.

The securing means is advantageously a paraocclusal tray, wherein the paraocclusal tray is placed on the teeth of the lower jaw and detachably connected to said teeth, wherein the at least one marker is placed on at least one arm of the paraocclusal tray projecting from the oral cavity, and wherein at least one receiving coil for generating the measurement data sets and/or the image data set is disposed in a region of the temporomandibular joints.

A paraocclusal tray is an arcuate, usually customized device that can be secured to the teeth of the upper jaw or the lower jaw by means of an adhesive, for example, as a result of which the paraocclusal tray follows the movement of the respective jaw. In the present case, the paraocclusal tray is made of a material, e.g. plastic, that adversely affects the magnetic resonance images as little as possible, for example by producing the weakest possible signals.

BRIEF DESCRIPTION OF THE DRAWINGS

Design examples of the invention are illustrated in the drawing. The figures show.

DESIGN EXAMPLES

Figure 1:
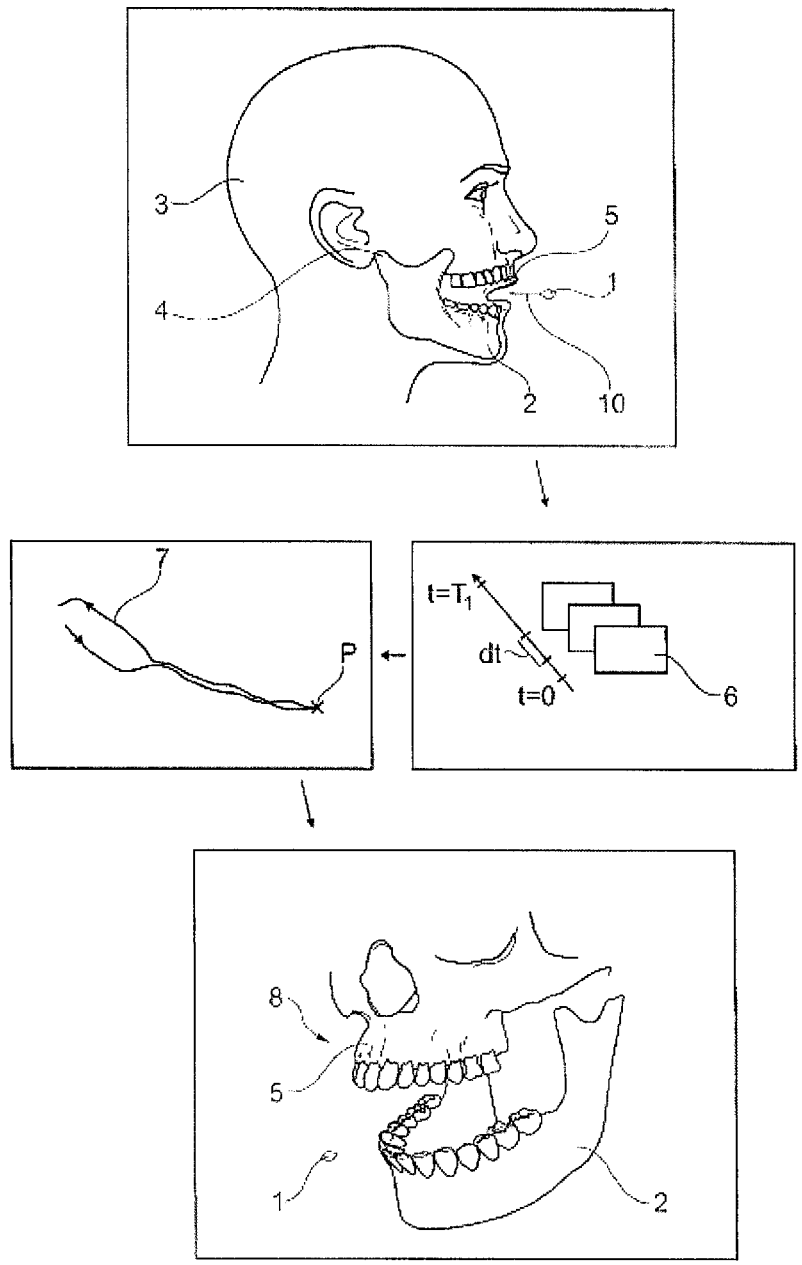
FIG. 1 method steps according to a first embodiment of the method according to the invention, FIG. 2 a schematic illustration of a lower jaw model moved relative to an upper jaw model.

FIG. 1 shows sketches of method steps of the method according to the invention according to a first embodiment. First, a marker 1 is secured to the lower jaw 2 of a patient 3 by means of a securing means 10. The marker 1 consists of a material visible to magnetic resonance imaging. In the illustrated design example, the securing means 10 is a paraocclusal tray that is secured to teeth of the lower jaw 2 by means of an adhesive.

A movement of the marker 1 caused by a movement of the temporomandibular joint 4 is subsequently measured using a magnetic resonance imagining device (not depicted), for which the lower jaw 2, the upper jaw 5 and the marker 1 are positioned in a recording volume of the recording device and the recording volume is measured. To do this, a plurality of measurement data sets 6 are generated by means of the magnetic resonance imaging device in short time intervals dt during a first measurement time interval T1. A three-dimensional position of the marker 1 at the time of generation of the respective measurement data set 6 is then identified on the basis of each measurement data set 6. The identified marker positions 1 as a function of the time t are stored as a marker movement curve 7. A point P is identified on the marker movement curve 7, whereby the point P corresponds to the first position P1 of the lower jaw relative to the upper jaw, e.g. the natural terminal occlusion.

Figure 2:
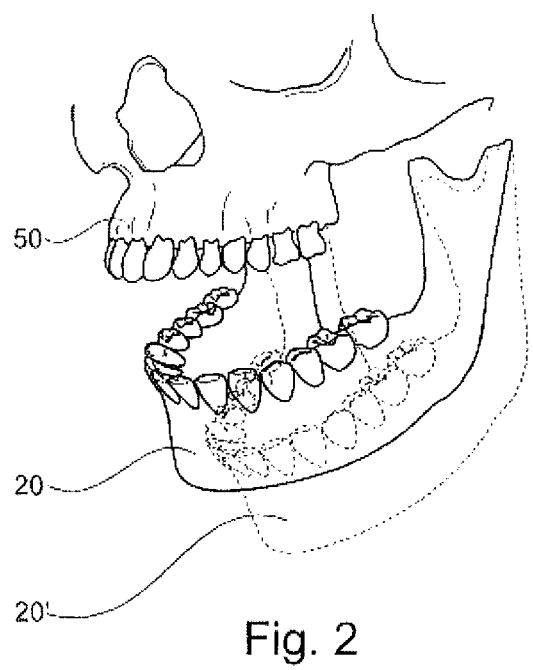

A visual image of the stationary jaw is subsequently created. To do this, an image data set 8 is generated according to the illustrated design example by means of the magnetic resonance imaging device during a second measurement time interval T2, whereby the lower jaw, the upper jaw and the marker remain in the recording volume of the recording device, and the lower jaw is in the first position 21 relative to the upper jaw, e.g. the natural terminal occlusion, or a position defined by a dental impression/bite block placed inside the mouth. In the illustrated design example, the image data set 8 comprises three-dimensional image information of the lower jaw 2, the upper jaw 5 and the marker 1. On the one hand, a three-dimensional lower jaw model as the second model 20 and a three-dimensional upper jaw model 50 as a first model 50 are produced on the basis of the image data set 8 by segmentation and are shown in FIG. 2. On the other hand, a relative position of the marker 1 to the lower jaw model 20 and the upper jaw model 50 is identified on the basis of the image data set. According to the illustrated design example, a three-dimensional position of the marker 1 in the recording volume is determined as well.

On the basis of the three-dimensional position of the marker 1 in the recording volume and the relative position of the marker 1 to the lower jaw model 20 and the upper jaw model 50, a movement path of the lower jaw model 20, 20' relative to the upper jaw model 50 is calculated from the marker movement curve 7 and visualized as sketched in FIG. 2.

The invention claimed is:

1. Method for detecting and displaying the movement of a temporomandibular joint of a patient with magnetic resonance imaging, comprising
    securing at least one marker that is visible to the magnetic resonance to the lower jaw of a patient by a securing measure,
    generating a plurality of magnetic resonance imaging measurement data sets of a recording volume in chronological succession during a first measurement time interval,
    positioning at least the temporomandibular joint, and/or at least a part of the lower jaw, as well as the at least one marker within the recording volume during the first measurement time interval,
    executing a movement of the lower jaw relative to the upper jaw during the first measurement time interval, where the movement of the lower jaw involves a first position relative to the upper jaw,
    identifying one at least two-dimensional marker position of the at least one marker in the recording volume in each measurement data set,
    producing a marker movement curve on the basis of the determined marker positions,
    identifying or knowing a point on the marker movement curve corresponding to the first position of the lower jaw relative to the upper jaw,
    generating at least one image data set of the recording volume during a second measurement time interval,
    positioning the at least the temporomandibular joint, and/or the at least a part of the lower jaw, as well as the at least one marker within the recording volume during the second measurement time interval, during the second measurement time interval, the lower jaw is in the first position relative to the upper jaw, identifying a first model, which displays at least a part of the upper jaw and/or a part of the temporal bone that comprises the temporomandibular joint socket (fossa mandibularis), and a second model, which displays at least a part of the lower jaw, from the image data set, determining a relative position of the at least one marker to the first model and to the second model from the image data set, and calculating a movement path of the second model relative to the first model and displaying the movement path on the basis of the marker movement curve and the relative position of the first model and the second model to the at least one marker.

2. Method according to claim 1, wherein each measurement data set comprises at least three 1D projection images or at least two 2D projection images.

3. Method according to claim 1, wherein each measurement data set comprises exactly one 1D projection image, and wherein one respective marker position is identified on the basis of at least two measurement data sets.

4. Method according to any claim 1, wherein the image data set is generated by magnetic resonance imaging.

5. Method according to claim 1, wherein the image data set is generated optically, and wherein the at least one marker is optically uniquely identifiable.

6. Method according to claim 1, wherein the image data set is generated by radiography, and wherein the at least one marker is radiopaque at least within a known range.

7. Method according to claim 1, wherein the at least one marker is a magnetic resonance imaging active marker or a magnetic resonance imaging semi-active marker.

8. Method according to claim 7, wherein the active or semi-active marker comprises a coil.

9. Method according to claim 8, wherein a body filled with a liquid is disposed within the coil.

10. Method according to claim 9, wherein the liquid is doped with a contrast agent.

11. Method according to claim 1, wherein the at least one marker comprises a three-dimensionally unique structure.

12. Method according to claim 1, wherein the at least one marker is placed within the oral cavity of a patient on a surface of at least one tooth or outside an oral cavity of a patient.

13. Method according to claim 1, wherein the securing measure is a paraocclusal tray, wherein the paraocclusal tray is placed on teeth of the lower jaw and is detachably connected to said teeth, wherein the at least one marker is placed on at least one arm of the paraocclusal tray projecting from an oral cavity of a patient and at least one receiving coil for producing the first measurement data sets and/or the image data set is disposed in a region around the temporomandibular joints.

* * * * *